(12) United States Patent
Jacquot et al.

(10) Patent No.: US 6,340,775 B1
(45) Date of Patent: Jan. 22, 2002

(54) METHOD FOR REDUCING A CARBONYL-CONTAINING COMPOUND

(75) Inventors: Roland Jacquot, Sainte Foy les Lyon; Michel Spagnol, Lyons, both of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/341,183

(22) PCT Filed: Jan. 6, 1998

(86) PCT No.: PCT/FR98/00010

§ 371 Date: Oct. 22, 1999

§ 102(e) Date: Oct. 22, 1999

(87) PCT Pub. No.: WO98/30517

PCT Pub. Date: Jul. 16, 1998

(30) Foreign Application Priority Data

Jan. 6, 1997 (FR) .............................. 97 00042

(51) Int. Cl.⁷ ..................... C07C 49/403; C07C 29/20; C07C 35/08
(52) U.S. Cl. ........................ 568/376; 568/835
(58) Field of Search ................. 568/376, 835

(56) References Cited

U.S. PATENT DOCUMENTS 3,980,718 A * 9/1976 Shabtai et al. .............. 502/62

OTHER PUBLICATIONS

Database CAPLUS on STN, Acc. No. 1967:121862, Kaye, 'Automatic recycling apparatus for elution chromatography: isolation fo cis–4–tert–butylcyclohexanol.' Mikrochim. Acta (1967), 2, pp. 322–327 (abstract).*

E.J. Creyghton et al, "Stereoselective reduction of 4–tert–butylcyclohexanone to cis–4–tert–butylcyclohexanol catalysed by zeolite BEA", Journal of the Chemical Society, Chemical Communications, No. 18, Sep. 21, 1995, Letchworth, GB, pp. 1859–1860, XP002038921.

* cited by examiner

Primary Examiner—Brian J. Davis
(74) Attorney, Agent, or Firm—Burns, Doane, Swecker & Mathis, L.L.P.

(57) ABSTRACT

A subject of the present invention is a process for the reduction of a carbonyl compound. More precisely, the invention relates to a process for reduction of an aldehyde and/or of a ketone. The reduction process of the invention, which consists of reacting a carbonyl compound with an alcohol in the presence of a zeolite catalyst, is characterized by the fact that it comprises: mixing, in any manner whatever, the carbonyl compound and the alcohol, passing said mixture over a catalyst bed containing at least one zeolite, subjecting the reaction mixture leaving the catalyst bed to recirculation over the catalyst bed, for a number of times that is sufficient to obtain the desired degree of conversion of the substrate.

43 Claims, 1 Drawing Sheet

METHOD FOR REDUCING A CARBONYL-CONTAINING COMPOUND

Figure 1:
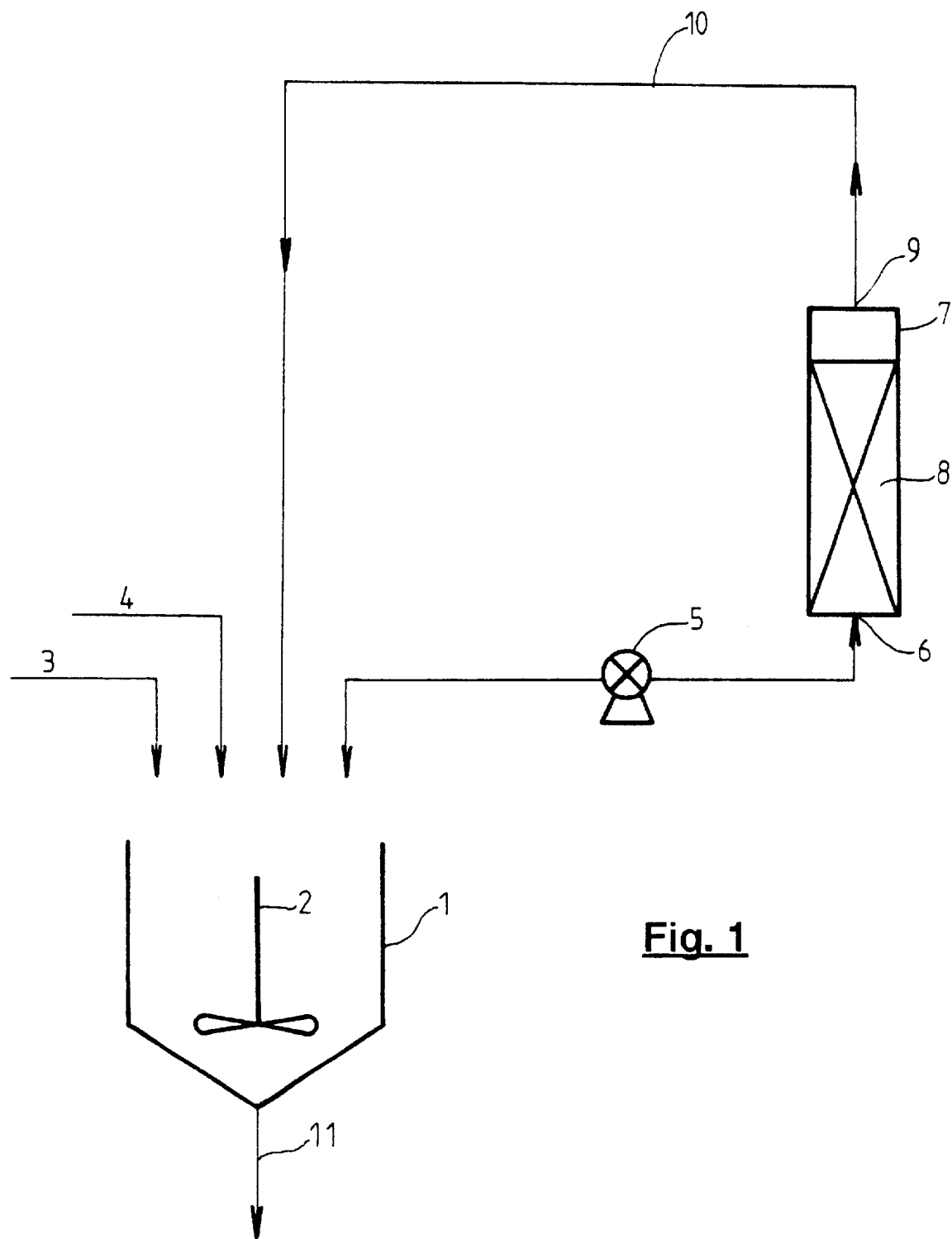

This application is a 371 of PCT/FR98/00010.

BACKGROUND OF THE INVENTION

1. Field of the Invention

A subject of the present invention is a process for reduction of a carbonyl compound. More precisely, the invention relates to a process for reduction of an aldehyde and/or of a ketone.

2. Description of Related Art

Various processes exist for reduction of carbonyl compounds to alcohols. In particular, reduction of aldehydes and ketones to alcohols by a hydrogenation process, in the presence of Raney nickel, is known.

The problem that arises is that the reduction of an aldehyde or of a ketone, carried out according to the aforesaid process, is a reaction that is not stereoselective, so that a mixture of stereo-isomers is obtained. This is the case when we carry out the reduction of a substituted cyclohexanone, thus resulting in a thermodynamic mixture of the stereo-isomers.

The objective of the present invention is to provide a simple reduction process that is applicable to any carbonyl compound, and more particularly to carbonyl compounds for which it is required to obtain a majority stereo-isomer.

Furthermore, Van Bekkum et al. have described the reduction of 4-tert.-butylcyclohexanone to cis-4-tert.-butylcyclohexanol, catalysed by a BEA zeofite [J. Chem. Soc., Chem. Commun., p. 1859–60 (1995)].

Use of the said catalyst on an industrial scale poses a problem because the productivity of the catalyst is inadequate and it would be necessary to have an extremely large reactor.

The aim of the present invention is to provide a process by which the aforesaid drawbacks can be obviated.

SUMMARY OF THE INVENTION

There has now been found, and this is what constitutes a subject of the present invention, a process for reduction of a carbonyl compound to the corresponding alcohol, by reaction of the said carbonyl compound with an alcohol in the presence of a zeolite catalyst, characterized by the fact that it comprises:

- mixing, in any manner whatever, the carbonyl compound and the alcohol,
- passing the said mixture over a catalyst bed containing at least one zeolite,
- subjecting the reaction mixture leaving the catalyst bed to recirculation over the catalyst bed, for a number of times that is sufficient to obtain the desired degree of conversion of the substrate.

BRIEF DESCRIPTION OF THE FIGURE OF THE DRAWING

The FIGURE is a flow diagram of the processor the invention

DETAILED DESCRIPTION OF PREFERRED EMBODIMENTS

In the process of the invention, we therefore employ a carbonyl compound, aldehyde or ketone and an alcohol.

More precisely, a subject of the present invention is a process for reduction of a carbonyl compound corresponding more particularly to general formula (I):

(I)

in the said formula (I):

$R_a$ and $R_b$, which are identical or different, represent a hydrogen atom or a monovalent hydrocarbon radical, substituted if necessary, possessing from 1 to 40 carbon atoms; at most one of the radicals $R_a$ or $R_b$ is a hydrogen atom, $R_a$ and $R_b$ can form a ring that optionally contains another heteroatom.

More precisely, $R_a$ and $R_b$ can represent a monovalent hydrocarbon radical, substituted or unsubstituted, which can be a saturated or unsaturated, linear or branched acyclic aliphatic radical; an aromatic, monocyclic or polycyclic, or saturated or unsaturated heterocyclic or carbocyclic radical.

$R_a$ and $R_b$ can have various meanings. Various examples are given below but in no case are they limitative.

In the compounds of formula (I), $R_a$ and $R_b$ preferably represent a saturated or unsaturated, linear or branched acyclic aliphatic radical possessing preferably from 1 to 12 carbon atoms, saturated or containing one to several unsaturated bonds on the chain, generally 1 to 3 unsaturated bonds which can be simple or conjugated double bonds or triple bonds.

More particularly, $R_a$ and $R_b$ represent a linear or branched alkyl, alkenyl or alkadienyl radical preferably possessing from 1 to 12 carbon atoms.

The hydrocarbon chain can if necessary:

be interrupted by one of the following groups Z:
—O—; —CO—; COO—; —NR$_1$—; —CO—NR$_1$—; —S—; —SO$_2$—; —NR$_1$—CO—; in the said formulae R$_1$ represents a hydrogen atom, a linear or branched alkyl group possessing from 1 to 6 carbon atoms, preferably a methyl or ethyl radical, and/or carries one of the following substituents:
—OH; —COOH; —COOX; —CO—N(R$_1$)(R$_2$); —COOR$_1$; —CHO; —COR$_1$; —NO$_2$; —X; —CF$_3$.
in these formulae, X represents a halogen atom, preferably an atom of chlorine or of bromine and R$_2$ has the same meaning as R$_1$ given previously.

It is equally possible for $R_a$ and $R_b$ to represent a saturated or unsaturated, linear or branched acyclic aliphatic radical, optionally carrying a cyclic substituent. Cycle or ring is intended to mean a carbocyclic or heterocyclic ring, saturated, unsaturated or aromatic.

The acyclic aliphatic radical can be joined to the ring by a valence bond or by one of the aforementioned groups Z.

As examples of cyclic substituents, there can be mentioned cycloaliphatic, aromatic or heterocyclic substituents, especially cycloaliphatic containing 6 carbon atoms in the ring or benzene substituents, these cyclic substituents themselves optionally carrying one or more substituents.

As examples of these radicals, among others there can be mentioned the benzyl radical.

In general formula (I), $R_a$ and $R_b$ can represent a monocyclic carbocyclic radical. The number of carbon atoms in the ring can vary widely from 3 to 8 carbon atoms but it is preferably equal to 5 or 6 carbon atoms.

The carbocycle can be saturated or can contain 1 or 2 unsaturated bonds in the ring, preferably from 1 to 2 double bonds.

As preferred examples of radicals $R_a$ and $R_b$, there can be mentioned cyclohexyl or cyclohexenyl radicals.

In the case when $R_a$ and $R_b$ represent a saturated or unsaturated monocyclic, carbocyclic radical, it is possible for one or more of the carbon atoms of the ring to be replaced by a heteroatom, preferably oxygen, nitrogen or sulphur or by a functional group, preferably carbonyl or ester, thus resulting in a monocyclic, heterocyclic compound. The number of atoms in the ring can vary widely from 3 to 8 atoms but it is preferably equal to 5 or 6 atoms.

Radicals $R_a$ and $R_b$ can also be carbocyclic, polycyclic, preferably bicyclic which means that at least two rings have two carbon atoms in common. In the case of polycyclic radicals, the number of carbon atoms in each ring varies between 3 and 6: the total number of carbon atoms is preferably equal to 7.

Examples of bicyclic structures commonly encountered are given below:

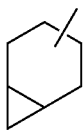   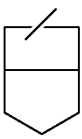

[4, 1, 0]    [2, 2, 1]    [3, 1, 1]    [3, 2, 0]

Radicals $R_a$ and $R_b$ can also be heterocyclic, polycyclic, preferably bicyclic which means that at least two rings have two atoms in common. In this case the number of atoms in each ring varies between 3 and 6 and is preferably equal to 5 or 6.

Radicals $R_a$ and $R_b$ can preferably represent an aromatic carbocyclic radical, and especially a benzene radical, corresponding to general formula (II):

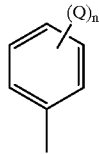

(II)

in this formula (II):

n is an integer from 0 to 5, preferably from 0 to 3,

Q represents $R_3$, one of the following groups or functions:

a linear or branched alkyl radical, possessing from 1 to 6 carbon atoms, preferably from 1 to 4 carbon atoms, such as methyl, ethyl, propyl, isopropyl, butyl, isobutyl, sec-butyl, tert-butyl, a linear or branched alkenyl radical possessing from 2 to 6 carbon atoms, preferably from 2 to 4 carbon atoms, such as vinyl, allyl, a linear or branched alkoxy radical with I to 6 carbon atoms, preferably from 1 to 4 carbon atoms such as the methoxy, ethoxy, propoxy, isopropoxy and butoxy radicals, an acyl group possessing from 2 to 6 carbon atoms, a radical with the formula:

—$R_5$—OH

—$R_5$—COO$R_7$

—$R_5$—CHO

—$R_5$—NO$_2$

—$R_5$—CN

—$R_5$—N($R_7$)($R_8$)

—$R_5$—CO—N($R_7$)($R_8$)

—$R_5$—SH

—$R_5$—X

—$R_5$—CF$_3$ in the said formulae, R5 represents a valence bond or a linear or branched, saturated or unsaturated divalent hydrocarbon radical, possessing from 1 to 6 carbon atoms, e.g. methylene, ethylene, propylene, isopropylene, isopropylidene; radicals $R_7$ and $R_8$, which may be identical or different, represent a hydrogen atom or a linear or branched alkyl radical possessing from 1 to 6 carbon atoms; X denotes a halogen atom, preferably an atom of chlorine, bromine or fluorine,

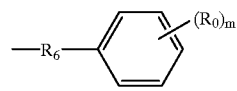

in which:

m is an integer from 0 to 5, preferably from 0 to 3, $R_0$ has the meaning given previously for $R_3$, $R_6$ represents a valence bond; a linear or branched, saturated or unsaturated divalent hydrocarbon group possessing from 1 to 6 carbon atoms such as e.g. methylene, ethylene, propylene, isopropylene, isopropylidene or one of the following groups designated Z: —O—; —CO—; COO—: —NR$_7$—; —CO—NR$_7$—; —S—; —SO$_2$—; —NR$_7$—CO—; in the said formulae $R_7$ represents a hydrogen atom, or a linear or branched alkyl group possessing from 1 to 6 carbon atoms, preferably a methyl or ethyl radical.

As examples of radicals $R_a$ and $R_b$ corresponding to formula (II), there can be mentioned more precisely the radicals phenyl, tolyl or xylyl, 1-methoxyphenyl, 2-nitrophenyl and the radicals biphenyl, 1,1'-methylenebiphenyl, 1,1'-isopropylidenebiphenyl, 1,1'-carboxybiphenyl, 1,1'-oxybiphenyl, 1,1'-iminobiphenyl: the said radicals can be substituted by one or more radicals Q as previously defined.

$R_a$ and $R_b$ can also represent a polycyclic aromatic hydrocarbon radical; the rings can form, together, ortho-condensed, ortho- and peri-condensed systems. More particularly, there can be mentioned a naphthalenic radical.

In general formula (I), $R_a$ and $R_b$ can also represent an aromatic heterocyclic radical, especially one with 5 or 6 atoms in the ring, of which 1 or 2 are heteroatoms such as atoms of nitrogen, sulphur and oxygen.

$R_a$ and $R_b$ can also represent a polycyclic aromatic heterocyclic radical, defined as being either a radical comprising at least 2 heterocycles, aromatic or not, containing at least one heteroatom in each ring and forming, between them, ortho- or ortho- and pericondensed systems or alternatively a radical comprising at least one hydrocarbon ring, aromatic or not, and at least one heterocycle, aromatic or not, forming between them ortho- or ortho- and pericondensed systems.

It should be noted that if the radical $R_a$ and $R_b$ contains any ring whatever, it is possible for this ring to contain a substituent. The substituent can be of any nature whatever provided it does not cause interference at the level of the desired product. The substituents most often carried by the ring are one or more alkyl or alkoxy radicals preferably possessing from 1 to 4 carbon atoms, preferably three methyl radicals, a methylene radical (corresponding to an exocyclic bond), an alkenyl radical, preferably an isopropenyl radical, a halogen atom, preferably chlorine or bromine.

Among all the radicals $R_a$ and $R_b$ mentioned previously, $R_a$ represents a phenyl radical optionally carrying an alkyl or alkoxy group possessing from 1 to 4 carbon atoms, a trihalomethyl group or a halogen atom and $R_b$ represents a hydrogen atom.

In formula (I), it is possible for $R_a$ and $R_b$ to form, together and with the carbon atom to which they are attached, a cyclic, monocyclic or polycyclic system.

Thus, the compound of formula (I) can be a cyclic ketone.

The number of carbonyl groups present in the starting substrate can therefore be greater than 1, for example equal to 2 and then we have a dione.

Given that the starting cyclic ketone employed in the process of the invention can be polycyclic, especially bicyclic, it follows that the number of carbonyl groups in the starting ketone compound can be equal to 3, or even to 4 or more.

The cyclic ketone employed in the process of the invention can therefore be a mono- or polycarbonylated ketone. It may be a monocyclic or polycyclic ketone.

The process of the invention is perfectly suitable for cyclic ketones corresponding to general formula (Ia):

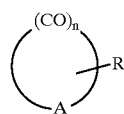

(Ia)

in which:
A denotes the residue of a ring forming all or part of a monocyclic or polycyclic system containing at least one carbonyl group,
R represents a hydrogen atom or one or more substituents, which may be identical or different,
n is a number preferably equal to 1 or 2.

It will be specified, though without limiting the scope of the invention, that the residue A optionally substituted represents preferably the residue:
of a saturated or unsaturated carbocyclic monocyclic compound,
of a polycyclic compound containing at least two carbocycles, saturated and/or unsaturated,
of a polycyclic compound containing at least two saturated and/or unsaturated rings: one or more of the carbon atoms optionally being replaced by a heteroatom,
of a polycyclic compound containing at least two carbocycles, one of which is aromatic.

The cyclic ketone of formula (Ia) can therefore be a monocyclic or polycyclic compound.

When it is a monocyclic compound, the number of carbon atoms in the ring can vary widely from 3 to 20 carbon atoms but is preferably 5 or 6 carbon atoms.

The carbocycle can be saturated or can contain 1 or 2 unsaturated bonds in the ring, preferably from 1 to 2 double bonds which are most often in the a position of the carbonyl group.

The compound can also be polycyclic, preferably bicyclic which means that at least two ring have two carbon atoms in common.

In the case of polycyclic compounds, the condensation to carbon of each ring is less pronounced, generally from 3 to 8 but is preferably equal to 5 or 6 carbon atoms.

The polycyclic compound can contain at least two saturated and/or unsaturated rings: one or more (preferably two) of the carbon atoms being replaceable by a heteroatom, preferably an atom of oxygen or nitrogen.

The polycyclic compound can contain at least two carbocycles, one of which is aromatic, the aromatic ring being preferably a benzene ring.

The cyclic ketone of formula (Ia) can bear one or more substituents.

The number of substituents present on the ring depends on the condensation to carbon of the ring, and on the presence or absence of unsaturated bonds on the ring.

The maximum number of substituents that can be carried by one ring is easily determined by a person skilled in the art.

As for the nature of the substituents, examples of substituents are given below but this list is not of a limitative character.

Any substituent whatever can be present on the ring provided it does not interfere at the level of the desired product. Examples are given below of substituents that can be carried by residue A:

R can represent $R_9$, one of the following groups:
a linear or branched acyclic aliphatic radical, possessing from 1 to 20 carbon atoms, saturated or containing one or more unsaturated bonds on the chain, preferably 1 to 3 unsaturated bonds which are preferably simple or conjugated double bonds; the hydrocarbon chain can optionally be:
interrupted by one of the following groups designated Z:
—O—; —CO—; COO—; —NR$_{10}$—; —CO—NR$_{10}$; —S—; —SO$_2$—;
in the said formulae $R_{10}$ represents a hydrogen atom, or a linear or branched alkyl radical possessing from 1 to 6 carbon atoms,
and/or carrying one of the following substituents:
OH; —CN; —N[R$_{10}$]$_2$; —COOR$_{10}$, —CF$_3$ or —X;
in the said formulae, the radicals $R_{10}$, which may be identical or different, represent a hydrogen atom or a linear or branched alkyl radical possessing from 1 to 6 carbon atoms and X represents a halogen atom, preferably fluorine, chlorine or bromine,
a radical of the type =$R_{11}$, in which $R_{11}$ represents an alkylidene radical possessing from 1 to 6 carbon atoms, a radical with the formula —C(CN)$_2$ or a cycloalkylidene or cycloalkenylidene radical possessing 5 or 6 carbon atoms or a benzylidene radical, optionally substituted, preferably by a halogen atom X,
a linear or branched alkoxy radical possessing from 1 to 6 carbon atoms,
two successive atoms of the ring can be joined together by an epoxy bridge or by a bridge of the alkylene dioxy type possessing from 1 to 4 carbon atoms, preferably the radicals methylene dioxy, ethylene dioxy, propylene dioxy,
an OH group,
a COOR$_{10}$ group, R$_{10}$ representing a hydrogen atom or an alkyl radical possessing from 1 to 6 carbon atoms, preferably methyl, ethyl, a CN group, a halogen atom, preferably fluorine, chlorine or bromine, a —$CF_3$— group.

R can represent $R_{12}$, one of the following more complex groups:

a saturated or unsaturated carbocyclic radical possessing from 4 to 7 carbon atoms, preferably a cyclopentyl, cyclohexyl, cyclopenten-2-yl, cyclopenten-3-yl, cyclohexen-1-yl, cyclohexen-2-yl, cyclohexen-3-yl radical, a radical with the formula

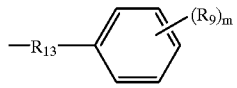

in which $R_{13}$ represents a valence bond or a linear or branched, saturated or unsaturated divalent hydrocarbon radical possessing from 1 to 6 carbon atoms, for example methylene, ethylene, propylene, isopropylene, isopropylidene and $R_9$ has the meaning given previously and m is an integer from 0 to 4, a radical —$R_{13}$—Z—$R_{14}$ in which Z and $R_{13}$ have the meaning given previously, $R_{14}$ represents a linear or branched alkyl radical possessing from 1 to 6 carbon atoms or a radical with the formula

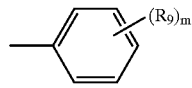

in which $R_9$ and m have the meaning given previously, a radical of the Spiro type with the formula:

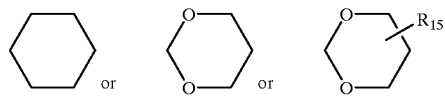

in which $R_{15}$ represents one or more linear or branched alkyl radicals possessing from 1 to 6 carbon atoms.

More precisely, in formula (Ia) the various symbols given previously can take the meanings given below.

A can represent the residue of a saturated monocyclic carbocyclic compound, possessing from 3 to 20 carbon atoms. One or two carbonyl groups may be present on the ring. The carbonyl group is preferably carried by a saturated carbocycle possessing 5 or 6 carbon atoms.

The saturated carbocycle can carry substituents. The number of substituents on each ring can vary widely from 1 to 5. It is generally 1 or 2.

The following may be mentioned as specific examples of substituents:

a linear or branched alkyl radical possessing from 1 to 15 carbon atoms, preferably a methyl, ethyl, n-propyl, isopropyl, n-butyl, sec-butyl, tert-butyl, n-pentyl, isopentyl, tert-pentyl, n-hexyl or n-heptyl radical, an alkyl radical possessing from 1 to 15 carbon atoms, carrying a functional group, preferably a function OH, CN, N[$R_{10}$]$_2$, COOR$_{10}$ with $R_{10}$, identical or different, representing a hydrogen atom, a linear or branched alkyl radical possessing from 1 to 6 carbon atoms: the alkyl chain optionally being interrupted by an oxygen atom or a carbonyl, carboxy or amino group, substituted if necessary, and there can be mentioned more particularly a radical with the formula —$NHCH_3$ or —$N(CH_3)_2$, a radical with the formula —$CH_2$—$CH_2$—CN, a radical with the formula —$CH_2$—CO—$(CH_2)_4$—COOH, a radical with the formula $COCH(CH_3)_2$, a radical with the formula —$(CH_2)_6$—COOH, a radical with the formula —$CH_2$—$COOCH_3$, a radical with the formula —$CH_2$—$COOC_2H_5$, a radical with the formula —$CH_2$—$CH_2$—$COOCH_3$, a radical with the formula —$(CH_2)_6$—$COOCH_3$, a radical with the formula —$(CH_2)_6$—$COOC_2H_5$, a radical with the formula —$(CH_2)_5$—$COOC_2H_5$, a radical with the formula —CO—$CH_3$, a radical with the formula —$C(CH_3)_2$—CO—$CH_3$, a radical with the formula —$CH_2$—$CH_2$—CO—$(CH_2)_4$—$CH_3$, an alkenylene or alkylidene radical, linear or branched, containing one or two double bonds possessing from 1 to 15 carbon atoms, preferably a radical with the formula —$CH_2$—CH=$CH_2$, a radical with the formula —$C(CH_3)$=$CH_2$, a radical with the formula —$CH_2$—CH=CH—$C_2H_5$, a radical with the formula —$CH_2$—CH=CH—$(CH_2)_2$—$CH_3$, a radical with the formula —CH=CH—$(CH_2)_4$—$CH_3$, a radical with the formula —$CH_2$—CH=$C(CH_3)_2$, a radical with the formula —$CH_2$—CH=$CCH_3$—$(CH_2)_2$—CH=$C(CH_3)_2$, a radical =$C(CH_3)_2$ or =CH—$(CH_2)_2$—$CH_3$, an alkenylene or alkylidene radical, linear or branched, containing one or two double bonds possessing from 1 to 15 carbon atoms, carrying a functional group, preferably a function OH, CN, $NH_2$, $COOR_{10}$ in which $R_{10}$ has the meaning given previously: the unsaturated chain optionally being interrupted by an oxygen atom, a carbonyl or carboxy group and there can be mentioned more especially a radical with the formula —$CH_2$—CH=CH—$(CH_2)_3$—COOH, a radical with the formula —CH=CH—$C(CH_3)$=CH—COOH, a radical with the formula —$CH_2$—CH=CH—$(CH_2)_3$—$COOCH_3$, a radical with the formula —CH=CH—$C(CH_3)$=CH—$COOCH_3$, a radical with the formula —CH=CH—CO—$CH_3$, a radical with the formula —CH=CH—CO—$(CH_2)_4$—$CH_3$ or a radical with the formula —CH=CH—CHOH—$(CH_2)_4$—$CH_3$, a linear or branched alkoxy radical possessing from 1 to 6 carbon atoms, preferably a methoxy or ethyoxy radical, two successive atoms of the ring can be joined together by an epoxy bridge or by a bridge such as the radicals methylene dioxy, ethylene dioxy, propylene dioxy, a radical of the spiro type with the formula

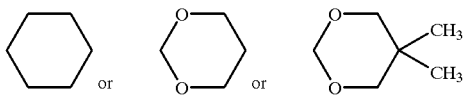

a radical with the formula

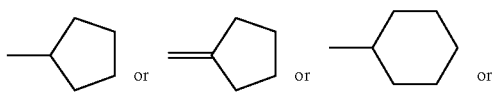

-continued

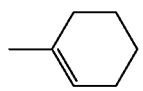

a radical with the formula

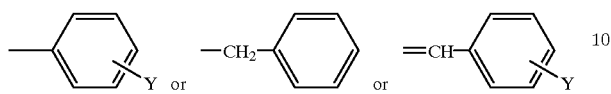

Y representing a hydrogen atom or a halogen atom, preferably fluorine or chlorine, a radical with the formula

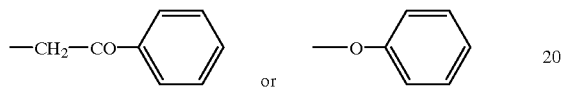

an OH group, a $COOR_{10}$ group, $R_{10}$ representing a hydrogen atom or an alkyl radical possessing from 1 to 6 carbon atoms, preferably methyl, ethyl, a CN group, a halogen atom, preferably fluorine, chlorine or bromine.

By way of illustration, there can be mentioned more particularly the compounds with the following formula:

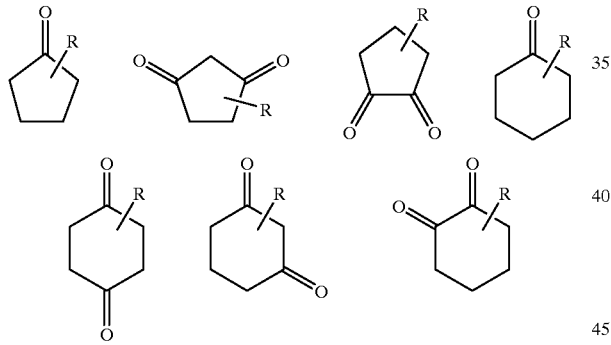

A can represent the residue of an unsaturated monocyclic carbocyclic compound possessing from 4 to 20 carbon atoms. One or two carbonyl groups may be present on the ring. The carbonyl group is preferably carried by an unsaturated carbocycle possessing 5 or 6 carbon atoms.

The unsaturated carbocycle can carry substituents. The number of substituents on each ring can vary widely from 1 to 5. It is generally 1 or 2.

The following may be mentioned as specific examples of substituents:
- a linear or branched alkyl radical possessing from 1 to 15 carbon atoms, preferably a methyl, ethyl, n-propyl, isopropyl, n-butyl, sec-butyl, tert-butyl, n-pentyl, isopentyl, tert-pentyl, n-hexyl or n-heptyl radical,
- an alkyl radical possessing from 1 to 15 carbon atoms, carrying a functional group, preferably a function OH, CN, $N[R_{10}]_2$, $COOR_{10}$ with $R_{10}$, which may be identical or different, representing a hydrogen atom, a linear or branched alkyl radical possessing from 1 to 6 carbon atoms; the alkyl chain can be interrupted by an oxygen atom or a carbonyl, carboxy or amino group, substituted if necessary, and there can be mentioned more particularly a radical with the formula —$NHCH_3$ or —$N(CH_3)_2$, a radical with the formula —$CH_2$—$CH_2$—CN, a radical with the formula —$CH_2$—CO—$(CH_2)_4$—COOH, a radical with the formula $COCH(CH_3)_2$, a radical with the formula —$(CH_2)_6$—COOH, a radical with the formula —$CH_2$—$COOCH_3$, a radical with the formula —$CH_2$—$COOC_2H_5$, a radical with the formula —$CH_2$—$CH_2$—$COOCH_3$, a radical with the formula —$(CH_2)_6$—$COOCH_3$, a radical with the formula —$(CH_2)_6$—$COOC_2H_5$, a radical with the formula —$(CH_2)_5$—$COOC_2H_5$, a radical with the formula —CO—$CH_3$, a radical with the formula —$C(CH_3)_2$—CO—$CH_3$, a radical with the formula —$CH_2$—$CH_2$—CO—$(CH_2)_4$—$CH_3$,
- an alkenylene or alkylidene radical, linear or branched, containing one or two double bonds possessing from 1 to 15 carbon atoms, preferably a radical with the formula —$CH_2$—CH=$CH_2$, a radical with the formula —$C(CH_3)$=$CH_2$, a radical with the formula —$CH_2$—CH=CH—$C_2H_5$, a radical with the formula —$CH_2$—CH=CH—$(CH_2)_2$—$CH_3$, a radical with the formula —CH=CH—$(CH_2)_4$—$CH_3$, a radical with the formula —$CH_2$—CH=$C(CH_3)_2$, a radical with the formula —$CH_2$—CH=$CCH_3$—$(CH_2)_2$—CH=$C(CH_3)_2$,
- a radical =$C(CH_3)_2$ or =CH—$(CH_2)_2$—$CH_3$,
- an alkenylene or alkylidene radical, linear or branched, containing one or two double bonds possessing from 1 to 15 carbon atoms, carrying a functional group, preferably a function OH, CN, $NH_2$, $COOR_{10}$ in which $R_{10}$ has the meaning given previously: the unsaturated chain can be interrupted by an oxygen atom, a carbonyl or carboxy group and there can be mentioned more especially a radical with the formula —$CH_2$—CH=CH—$(CH_2)_3$—COOH, a radical with the formula —CH=CH—$C(CH_3)$=CH—COOH, a radical with the formula —$CH_2$—CH=CH—$(CH_2)_3$—$COOCH_3$, a radical with the formula —CH=CH—C$(CH_3)$=CH—$COOCH_3$, a radical with the formula —CH=CH—CO—$CH_3$, a radical with the formula —CH=CH—CO—$(CH_2)_4$—$CH_3$ or a radical with the formula —CH=CH—CHOH—$(CH_2)_4$—$CH_3$,
- a linear or branched alkoxy radical possessing from 1 to 6 carbon atoms, preferably a methoxy or ethoxy radical,
- a radical with the formula

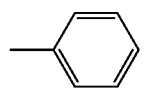

- an OH group,
- a group $COOR_{10}$, $R_{10}$ representing a hydrogen atom or an alkyl radical possessing from 1 to 6 carbon atoms, preferably methyl, ethyl,
- a halogen atom, preferably fluorine, chlorine or bromine.

By way of illustration, there can be mentioned more particularly the compounds with the following formula:

A can represent the residue of a polycyclic carbocyclic compound, preferably bicyclic, containing two saturated carbocycles, each preferably possessing from 4 to 8 carbon atoms. A carbonyl group may be present on one or both rings. It is also possible for two carbonyl groups to be present on the same ring. The carbonyl group is preferably carried by one or two saturated carbocycles possessing 5 or 6 carbon atoms.

In these polycyclic compounds, one or more carbon atoms, preferably two, can be replaced by a heteroatom, preferably an atom of nitrogen or oxygen.

The ring or rings of this polycyclic compound can carry substituents. The number of substituents on each ring is generally from 1 to 4, preferably 1 or 2. The following may be mentioned as examples of substituents that are commonly encountered:

- a linear or branched alkyl radical possessing from 1 to 6 carbon atoms, preferably a methyl or isopropyl radical,
- a radical with the formula —CH$_2$Br,
- a linear or branched alkoxy radical possessing from 1 to 6 carbon atoms, preferably a methoxy radical,
- a radical with the formula =CH$_2$,
- an OH group
- a —COOH group,
- a halogen atom, preferably fluorine, chlorine or bromine,
- a CF$_3$ group By way of illustration, compounds with the following formulae can be mentioned more particularly:

A can represent the residue of a bicyclic carbocyclic compound containing two carbocycles, each preferably possessing from 4 to 7 carbon atoms, one saturated the other unsaturated, generally with just one double bond. The carbonyl group can occur either in the saturated or in the unsaturated ring or on both. The carbonyl group is preferably carried by a saturated or unsaturated carbocycle, possessing 5 or 6 carbon atoms.

The ring or rings of this polycyclic compound can carry substituents. The number of substituents on each ring is generally from 1 to 3, preferably 1 or 2.

The following may be mentioned as specific examples of substituents:

- a linear or branched alkyl radical possessing from 1 to 6 carbon atoms, preferably a methyl radical,
- a radical with the formula $$-\underset{\underset{CH_3}{|}}{C}=CH_2,$$

- a radical with the formula —CH$_2$—O—CH$_3$,
- a halogen atom, preferably chlorine.

By way of illustration, compounds with the following formulae may be mentioned more particularly:

A can represent the residue of a polycyclic carbocyclic compound, preferably bicyclic, containing two unsaturated carbocycles, each preferably possessing 5 or 6 carbon atoms. A carbonyl group may be present on one of the two rings.

In these polycyclic compounds, one or more carbon atoms, preferably two, can be replaced by a heteroatom, preferably an atom of nitrogen or oxygen.

The ring or rings of this polycyclic compound can carry substituents. The number of substituents on each ring is generally from 1 to 5, preferably 1 or 2.

Generally, the substituents are one or more linear or branched alkyl radicals possessing from 1 to 6 carbon atoms, preferably a methyl or ethyl radical.

By way of illustration, compounds with the following formulae may be mentioned more particularly:

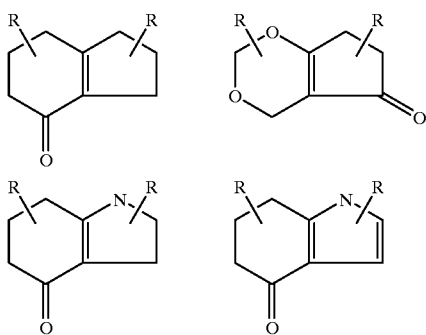

A can represent the residue of a polycyclic carbocyclic compound containing at least one aromatic carbocycle, preferably a benzene ring and a carbocycle preferably possessing from 4 to 7 carbon atoms and containing one or two carbonyl groups.

A is preferably the residue of a bicyclic compound containing a benzene ring and a carbocycle of 5 or 6 carbon atoms containing one or two carbonyl groups.

The two rings of this bicyclic radical can carry substituents. The number of substituents on each ring is generally 1 or 2.

As specific examples of substituents there can be mentioned:
a linear or branched alkyl radical possessing from 1 to 6 carbon atoms, preferably
a methyl or tert-butyl radical,
a radical with the formula

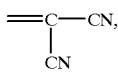

a linear or branched alkoxy radical possessing from 1 to 6 carbon atoms, preferably a methoxy radical,
a linear or branched alkoxy radical possessing from 1 to 6 carbon atoms, carrying other functional groups, for example a group OH and/or $N[R_{10}]_2$ with $R_{10}$, which may be identical or different, representing a hydrogen atom, a linear or branched alkyl radical possessing from 1 to 6 carbon atoms, preferably a radical with the formula —O—$CH_2$—CHOH—$CH_2$—NHBu-t
an OH group,
an acyl group possessing from 2 to 6 carbon atoms, preferably an acetyl, radical or a radical with the formula —CO—tert-butyl,
a group —$CH_2$—COOH,
a group —$NH_2$,
a halogen atom, preferably fluorine, chlorine or bromine.

By way of illustration, there can be mentioned, more particularly, compounds with the following formulae:

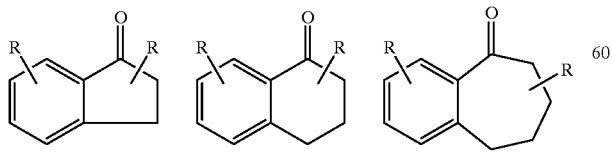

Among all the aforementioned cyclic ketone compounds, the process of the invention applies more particularly to saturated or unsaturated carbocyclic ketone compounds, possessing from 5 to 6 carbon atoms in the ring and corresponding to formula (Ia) in which:

R represents a hydrogen atom, or a linear or branched alkyl or alkoxy radical, possessing from 1 to 6 carbon atoms, preferably from 1 to 4 carbon atoms, or a benzylidene radical optionally carrying a halogen atom, n is equal to 1.

The cyclic ketones corresponding to formula (Ia), employed for preference in the process of the invention, are chosen among:
those in which the residue A in formula (Ia) represents the residue of a saturated monocyclic compound containing just one carbonyl group, such as:
cyclobutanone,
cyclopentanone,
2-methylcyclopentanone,
3-methylcyclopentanone,
2-methyl-2-carboxymethylcyclopentanone,
2,2-dimethylcyclopentanone
2-(2-octenyl)-cyclopentanone,
2-(3,7-dimethyl-2,6-octadienyl)cyclopentanone,
2-cyclopentylidenecyclopentanone,
2-benzylidenecyclopentanone,
2-[(p-chloro)benzylidene]cyclopentanone,
2-methyl-2-carboxymethyl-5-[(p-chloro)benzylidene] cyclopentanone,
2,4-dimethylcyclopentanone,
2,5-dimethylcyclopentanone,
3,4-dimethylcyclopentanone,
2,2,4-trimethylcyclopentanone,
4-methylcyclohexanone,
4-tert-butylcyclohexanone,
5-methyl-2-(1-methylethylidene)-cyclohexanone,
6-ketoprostaglandin E1,
methylester prostaglandin E2,
prostaglandin D2,
cyclohexanone,
3-methylcyclohexanone,
4-methylcyclohexanone,
4-tert-butylcyclohexanone,
4-n-pentylcyclohexanone,
2-benzylidenecyclohexanone,
2-(N,N,-dimethylamino)cyclohexanone,
3,5-dimethylcyclohexanone,
dihydrocarvone,
cycloheptanone,
cyclooctanone,
cycloheptadecanone,
those in which the residue A in formula (Ia) represents the residue of a saturated monocyclic compound containing two carbonyl groups, such as:
1,3-cyclopentanedione,
2-allyl-2-methyl-1,3-cyclopentanedione,
3,3-dimethyl-1,2-cyclopentanedione,
3,4-dimethyl-1,2-cyclopentanedione,
1,2-cyclohexanedione,
1,3-cyclohexanedione,
1,4-cyclohexanedione,
1,2-cycloheptanedione,
those in which the residue A in formula (Ia) represents the residue of an unsaturated monocyclic compound containing just one carbonyl group, such as:
2-cyclopentenone,
3-methyl-2-cyclopentenone,
4,4-dimethyl-2-cyclopentenone, 2-pentyl-2-cyclopentenone,
3-ethoxy-2-cyclopentenone,
2-hydroxy-3-ethyl-2-cyclopentenone,
prostaglandin J2,
jasmone,
2-hydroxy-3,4-dimethyl-2-cyclopentenone,
15-oxoprostaglandin E2,
2-ethoxy-2-cyclohexenone,
3-bromo-2-cyclohexenone,
carvone,
8-hydroxycarvotanacetone
2-methyl-5-(1-methylethenyl)-2-cyclohexenone,
3,5,5-trimethyl-2-cyclohexenone,
methyl ester of abscisic acid,
2-hydroxy-3-methyl-6-(1-methylethyl)-2-cyclohexenone,
5-cyclohexadecenone.
those in which residue A in formula (Ia) represents the residue of an unsaturated monocyclic compound containing two carbonyl groups, such as:
2-cyclopentene-1,4-dione,
4-hydroxy-5-methyl4-cyclopentene-1,3-dione,
those in which residue A in formula (Ia) represents the residue of a saturated bicyclic compound containing one or two carbonyl groups, such as:
isobornylcyclohexanone,
isofenchylcyclohexanone,
isocamphylcyclohexanone,
bornylcyclohexanone,
fenchylcyclohexanone,
camphylcyclohexanone,
camphor,
norcamphor,
3-bromocamphor,
2,3-bornanedione,
1-decalone,
2-decalone,
N-(ethoxycarbonyl)nortropinone,
those in which residue A in formula (Ia) represents the residue of a saturated/unsaturated bicyclic compound containing one or two carbonyl groups, such as:
bicyclo[3.2.0]hept-2-en-6-one,
1-(methoxymethyl)-bicyclo[2.2.0]hept-5-en-2-one,
3,4,8,8a-tetrahydro-8a-methyl-1,6(2H,7H)-naphthalenedione.
those in which residue A in formula (Ia) represents the residue of an unsaturated bicyclic compound containing a carbonyl group, such as:
6,7-dihydro-cyclopenta-1,3-dioxin-5(4H)-one,
6,7-dihydro-1,1,2,3,3-pentamethyl4(5H)-indanone,
4-oxo-4,5,6,7-tetrahydroindole.
those in which residue A in formula (Ia) represents the residue of a bicyclic compound one of which is aromatic containing one or two carbonyl groups, such as:
2-indanone,
2-methyl-1-indanone,
4-methyl-1-indanone,
4-methoxy-1-indanone,
6-methoxy-1-indanone,
4-hydroxy-1-indanone,
5-bromo-1-indanone,
1,3-indanedione,
1-tetralone,
2-tetralone,
4-methyl-1-tetralone,
5,7-dimethyl-1-tetralone,
5-methoxy-1-tetralone,
6,7-dimethoxy-1-tetralone,
5-hydroxy-1-tetralone,
levobunolol.

Among all the compounds of formula (I) that can be used in the process of the invention, the following compounds are employed more particularly:
benzaldehyde,
anisaldehyde,
4-chlorobenzaldehyde,
veratric aldehyde,
cinnamic aldehyde,
α-naphthylaldehyde,
isobornylcyclohexanone,
isofenchylcyclohexanone,
isocamphylcyclohexanone,
bornylcyclohexanone,
fenchylcyclohexanone,
camphylcyclohexanone,
4-methylcyclohexanone,
4-tert-butylcyclohexanone.

As for the alcohol used, it is a compound that permits transfer of the hydride onto the carbonyl group.

More particularly it corresponds to formula (III):

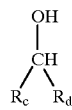

(III)

in formula (III):
$R_c$ and $R_d$ have the meaning given previously for $R_a$ and $R_b$ in formula (I).

It is preferably an aliphatic or cycloaliphatic, secondary or tertiary alcohol.

In view of the fact that this reactant is consumed during the reaction, it should be as cheap as possible. That is why it is preferable to employ alcohols that have low condensation to carbon, preferably less than 6 carbon atoms and, even more preferred, less than 4 carbon atoms.

As more specific examples of alcohols suitable for application of the invention, among others there can be mentioned isopropanol, isobutanol, sec-butanol, tert-butanol and glycerol.

The alcohol used preferably is isopropanol.

In accordance with the invention, the reaction of reduction is carried out in the presence of a zeolite catalyst.

"Zeolite" is taken to mean a crystallized tectosilicate of natural or synthetic origin whose crystals result from the three-dimensional arrangement of tetrahedral units of $SiO_4$ and $TO_4$, where T represents a trivalent element such as aluminium, gallium, boron, iron, preferably aluminium.

Zeolites of the aluminosilicate type are the commonest.

Zeolites have, within the crystal lattice, a system of cavities that are interconnected by channels with a well-defined diameter, which are called pores.

Zeolites can have a one-dimensional, two-dimensional or three-dimensional network of channels.

A natural or synthetic zeolite can be employed in the process of the invention.

The following may be mentioned as examples of natural zeolites that can be used: chabazite, clinoptilolite, erionite, phillipsite, offretite.

Synthetic zeolites are perfectly suitable for use in the invention.

As examples of synthetic zeolites with a one-dimensional network, the following may be mentioned among others: zeolite ZSM-4, zeolite L, zeolite ZSM-12, zeolite ZSM-22, zeolite ZSM-23, zeolite ZSM-48.

As examples of zeolites with a two-dimensional network that are used preferentially, there can be mentioned mordenite and ferrierite.

With regard to zeolites with a three-dimensional network, there can be mentioned, more particularly, zeolite β, zeolite Y, zeolite X, zeolite ZSM-5, zeolite ZSM-11, offretite.

Preference is given to the use of synthetic zeolites and more particularly to zeolites in the following forms:

mazzite with molar ratio Si/Al of 3.4, zeolite L with molar ratio Si/Al from 1.5 to 3.5, mordenite with molar ratio Si/Al from 5 to 15, ferrierite with molar ratio Si/Al from 3 to 10, offretite with molar ratio Si/Al from 4 to 8.5, β zeolites with molar ratio Si/Al greater than 8, generally between 10 and 100, preferably between 12 and 50, and even more preferred between 12 and 35, β zeolites containing titanium with Si/Al ratio greater than 100, preferably between 200 and 600 and with Ti content expressed as percentage by weight of $TiO_2$ varying between 0.1 and 10%, preferably between 1 and 5%, Y zeolites and in particular zeolites obtained after dealumination treatment (for example hydro-treatment, washing using hydrochloric acid or treatment with $SiCl_4$) and there can be mentioned more particularly the US-Y zeolites with molar ratio Si/Al above 2, preferably between 6 and 60;

X zeolite of the faujasite type with molar ratio Si/Al from 0.7 to 1.5, zeolites ZSM-5 or aluminium silicalite with molar ratio Si/Al from 10 to 500.

zeolite ZSM-11 with molar ratio Si/Al from 5 to 30, mesoporous zeolite of the MCM type, more particularly MCM-22 and MCM-41 with molar ratio Si/Al between 10 and 100, preferably between 15 and 40.

Among all these zeolites, in the process of the invention preference is given to the use of β and Y zeolites.

Whatever the nature of the zeolite, in order to obtain the desired Si/Al ratio it may be necessary to effect a dealumination treatment.

Thus, it is possible to employ methods that are known to a person skilled in the art, and among these there can be mentioned, as non-exhaustive examples, calcinations in the presence of vapour, calcinations in the presence of steam followed by treatment with inorganic acids ($HNO_3$, HCl etc.), direct dealumination treatments by reagents such as silicon tetrachloride ($SiCl_4$), ammonium hexafluorosilicate $((NH_4)_2SiF_6)$, ethylenediamine-tetracetic acid (EDTA) as well as its mono- or disodium form. A dealumination treatment can also be carried out by direct acid attack by solutions of inorganic acids, such as hydrochloric acid, nitric acid, sulphuric acid or organic acids, such as in particular acetic acid and oxalic acid.

Moreover, any combination of the aforementioned dealumination methods is also possible.

One variant of the invention consists of employing a zeolite that has undergone activation by calcination. The operation of calcination is carried out at a temperature between 200° C. and 700° C., preferably between 400° C. and 600° C., for a time varying from 1 to 24 hours, preferably from 5 to 8 hours.

The zeolites employed in the process of the invention are known products that are described in the literature [cf. Atlas of zeolites structure types by W. M. Meier and D. H. Olson published by the Structure Commission of the International Zeolite Association (1978)].

It is possible to use commercially available zeolites or they can be synthesized according to the processes described in the literature.

Reference may be made to the aforementioned Atlas, and more particularly, for the preparation:

of zeolite L to the work of Barrer R. M. et al., Z. Kristallogr., 128, pp. 352 (1969), of zeolite ZSM-12, to U.S. Pat. No. 3,832,449 and the article by LaPierre et al., Zeolites 5, p. 346 (1985), of zeol te ZSM-22, to the work of Kokotallo G. T. et al., Zeolites 5, p. 349 (1985), of zeolite ZSM-28, to U.S. Pat. No. 4,076,842 and the article by Rohrman A. C. et al., Zeolites 5, p. 352 (1985), of zeolite ZSM-48, to the works of Schlenker J. L. et al., Zeolites 5, p. 355 (1985), of β zeolite to U.S. Pat. No. 3,308,069 and the article by Caullet P. et al., Zeolites 12, p. 240 (1982), of titanium-containing β zeolites, to patents FR 2 730 723 and FR 2 730 722, of mordenite, to the works of Itabashi et al., Zeolites 6, p. 30 (1986), of X and Y zeolites to U.S. Pat. No. 2,882,244 and U.S. Pat. No. 3,130,007 respectively, of zeolite ZSM-5, to U.S. Pat. No. 3,702,886 and the article by Shiralker V. P. et al., Zeolites 9, p. 363 (1989), of zeolite ZSM-11, to the works of Harrison I. D. et al., Zeolites 7, p. 21 (1987), of mesoporous, type MCM zeolite, to the article by Beck et al., J. Am. Chem. Soc., 114 (27), p. 10834–43 (1992).

The zeolite constitutes the catalyst phase. It can be used alone or mixed with a mineral matrix. In the description, "catalyst" will be used to designate the catalyst made entirely of zeolite or mixed with a matrix prepared according to the techniques known to a person skilled in the art.

For this purpose, the matrix can be chosen among the oxides of metals, such as oxides of aluminium, silicon and/or zirconium, or alternatively among the clays and more especially kaolin, talc or montmorillonite.

In the catalyst, the content of active phase represents from 5 to 100% of the weight of the catalyst.

The catalysts can be used in various forms in the process of the invention: powder, shaped products such as granules (for example, extrusions or spheres), tablets that are obtained by extrusion, moulding, compacting or any other type of known process. In practice, on an industrial scale, the forms as granules or spheres offer more advantages both in terms of efficacy and in terms of convenience of use.

In accordance with the invention, the reaction of reduction is carried out according to a process of recirculation of the reaction mixture over a fixed bed of catalyst.

The process begins with mixing the carbonyl compound and the alcohol, in any manner whatever.

Thus, it is possible to mix the carbonyl compound and the alcohol in a mixing zone, and then send the mixture obtained over the catalyst bed.

According to another variant, one of the reactants (carbonyl compound or alcohol) can be introduced and sent over the catalyst bed then the other reactant is added, in one go or progressively when the desired reaction temperature is reached. In this variant, preferably the carbonyl compound is introduced, then the alcohol is added progressively.

Still within the scope of the invention, a mixture of reactants is introduced and then one of the other two reactants is added, at the desired temperature, in such a way that the desired carbonyl compound/alcohol ratio is obtained.

The final ratio between the number of moles of carbonyl compound and the number of moles of alcohol can vary widely. Thus, the ratio can range from 0.1 to 20, and is preferably between 0.5 and 4.0.

A preferred form of the invention consists of employing an excess of carbonyl compound, so as to increase the yield while maintaining the activity of the catalyst. Thus, we choose a molar ratio of carbonyl compound/alcohol equal to at least 1, preferably between 1 and 20 and even better between 1 and 10.

One of the reactants is generally used as a reactive solvent but the invention does not exclude the use of an organic solvent, the nature of which is determined by a person skilled in the art.

According to a preferred manner of carrying out the process of the invention, the temperature of the mixture is raised to the temperature at which the reaction is carried out.

The temperature at which the reaction of reduction is applied depends on the reactivity of the starting substrate and on that of the alcohol.

It is between 20° C. and 200° C., and preferably between 40° C. and 150° C.

The reactants are passed over a catalyst bed containing at least one zeolite.

The quantity of catalyst that is employed in the process of the invention can vary over a wide range.

The catalyst can represent, by weight in relation to the carbonyl compound used, from 0.01 to 50%, and preferably from 1.0 to 20%.

Generally the reaction is carried out at atmospheric pressure but lower or higher pressures may also be suitable. Operation is under autogenous pressure when the reaction temperature is above the boiling point of the reactants and/or products.

The reaction mixture passes through the catalyst bed, preferably from bottom to top, and at the exit it is sent to the zone where the reactants are mixed, so that it can be recycled a sufficient number of times to obtain the desired degree of conversion of the substrate, preferably above 20%, and even better between 50 and 100%. The degree of conversion of the substrate is defined as the ratio of the number of moles of substrate converted to the number of moles of substrate introduced.

The linear flow rate of liquid through the catalyst bed varies advantageously between 0.1 and 10 cm/s, and preferably between 0.1 and 5 cm/s.

The residence time of the material flowing through the catalyst bed varies, for example, between 15 min and 15 h, and preferably between 30 min and 10 h.

At the end of reaction, we obtain a liquid phase containing an alcohol which can be recovered in the conventional manner, by distillation or by recrystallization from a suitable solvent, after first eliminating the excess reactants.

For better understanding of the invention, a preferred manner of carrying out the invention is shown in the accompanying FIG. 1.

The carbonyl compound, preferably a ketone, and the alcohol are mixed in reactor (1). The reactor, with or without stirrer, is equipped with valves for supplying the reactants and for emptying, and is equipped with a heating device or is provided with a double jacket for heating the mixture by circulating a liquid at a suitable temperature. Stirring, which is not obligatory, can be effected using an Impeller® stirrer (2).

The carbonyl compound preferably a ketone (3) and the alcohol (4) are fed into reactor (1).

The reaction mixture is sent by any appropriate means, especially a centrifugal pump (5), at (6) to the base of a tubular reactor (7) containing the solid zeolite catalyst in a fixed bed (8).

At reactor outlet (9), the reaction mixture is conveyed by means of a pipe (10) in reactor (1) and thus circulates in a closed loop.

At the end of reaction, the reaction mixture is recovered by emptying mixer (1) by means of a valve (11), which is not shown in the diagram.

The process of the invention is particularly well suited for the preparation of mixtures of cis or trans isomers of substituted cyclohexanol, preferably with substitution in the para position relative to the hydroxyl group, containing at least 90% and preferably at least 95% of the cis or trans isomer: the substituent is preferably an aliphatic or cycloaliphatic alkyl group, possessing from 1 to 12 carbon atoms, preferably from 1 to 4.

The invention is perfectly suitable for the preparation of mixtures of isomers of 4-methylcyclohexanol or 4-tert-butylcyclohexanol, containing at least 90%, and preferably at least 95% of the cis isomer.

The following examples illustrate the invention but without limiting it.

In the examples, the yields stated correspond to the following definition:

$$\text{Yield: } RR_{A.A.} = \frac{\text{number of moles of alcohol formed}}{\text{number of moles of ketone introduced}} \%$$

EXAMPLES

The operating procedure followed in the various examples is given below, referring to FIG. 1.

A stainless-steal reactor (7) is loaded with the zeolite catalyst to form the catalyst bed which rests on a thickness (approx. 20 mm) of glass spheres so that the height of the bed that is covered with about 20 mm of glass spheres with diameter of 5mm.

A 3-litre double-jacket Sovirel® reactor (1) is loaded with the ketone (3) and isopropanol (4), at room temperature.

It is stirred (about 500 rev/min) and a homogeneous solution is obtained.

This solution is heated with reflux and this solution is made to circulate through the fixed bed at a flow rate of 60 l/h.

The flow rate is maintained throughout the reaction time.

At the end of reaction, recirculation through the fixed bed is stopped and the reaction mixture is left to cool.

The reaction mixture is then distilled to recover the solvent and the alcohols that formed.

Example 1

Reduction of 4-methylcyclohexanone is carried out in this example.

The catalyst used contains 40% of binder (alumina) and 60% of a β zeolite sold by the company PQ.

The zeolite used is a zeolite with "Si/Al" ratio of 12.5.

It is used at the rate of 20% by weight relative to the 4-methylcyclohexanone, i.e. 92 g.

The number of moles of isopropanol used is 8 times greater than that of the ketone.

The reaction temperature is 80° C.

Using gas chromatography, a yield (RR) of 99.6% of cyclohexane alcohols is determined after 5 h of reaction, and a selectivity (RT) for cis 4-methylcyclohexanol of 96.8%.

Examples 2 to 3

On the same catalyst bed as previously, this operation is repeated twice.

To obtain the same results as before, the reaction times are 8 h and 12 h 30, respectively.

Example 4

The catalyst used previously is employed, after calcining for 18 h at 500° C.

After reaction for 5 h 15, a yield (RR) of 99.5% of cyclohexane alcohols and a selectivity (RT) of 95.8% for cis 4-methylcyclohexanol are determined by gas chromatography.

Example 5

Reduction of 4-tert-butylcyclohexanone is carried out in this example.

The same catalyst is used as in example 1.

It is used at the rate of 25% by weight relative to the 4-tert-butylcyclohexanone, i.e. 105 g.

The number of moles of isopropanol used is 10 times greater than that of the ketone.

The temperature is the same as in example 1.

A yield (RR) of 4-tert-butylcyclohexane alcohols of 99.1% and a selectivity (RT) for cis 4-tert-butylcyclohexanol of 97.1% are determined by gas chromatography.

Example 6

Example 1 is reproduced but using an extruded HY zeolite containing 40% of alumina as binder: the Si/Al ratio is 10.

In this case, the yield of cyclohexane alcohols is 98% and the selectivity for trans 4-methylcyclohexanol is 92%.

Example 7

Example 1 is reproduced but using a mesoporous zeolite MCM22.

In this case, the yield of cyclohexane alcohols is 85% and the selectivity for trans 4-methylcyclohexanol is 86%.

Example 8

Example 1 is reproduced but using a titanium-containing β zeolite.

In this case the yield of cyclohexane alcohols is 95% and the selectivity for cis 4-methylcyclohexanol is 98%.

What is claimed is:

1. A process for reduction of a carbonyl compound to the corresponding alcohol, by reaction of said carbonyl compound with an alcohol in the presence of a zeolite catalyst, comprising:

mixing, in any manner whatever, the carbonyl compound and the alcohol, passing said mixture over a catalyst bed containing at least one zeolite, subjecting the reaction mixture leaving the catalyst bed to recirculation through the catalyst bed, for a number of times sufficient to obtain the desired degree of conversion of the substrate.

2. A process according to claim 1, wherein the carbonyl compound corresponds to formula (1):

(I)

in said formula (I):

$R_a$ and $R_b$, which may be identical or different, represent a hydrogen atom or a monovalent hydrocarbon radical, optionally substituted, possessing from 1 to 40 carbon atoms; at most one of the radicals $R_a$ and $R_b$ is a hydrogen atom, $R_a$ and $R_b$ can form a ring, optionally containing another heteroatom.

3. A process according to claim 2, wherein the carbonyl compound corresponds to formula (I) in which $R_a$ and $R_b$ represent a monovalent hydrocarbon radical, substituted or not, which can be a saturated or unsaturated, linear or branched acyclic aliphatic radical; a monocyclic or polycyclic, saturated, unsaturated or aromatic heterocyclic or carbocyclic radical.

4. A process according to claim 2, wherein the carbonyl compound corresponds to formula (I) in which $R_a$ and $R_b$ represent a saturated or unsaturated, linear or branched acyclic aliphatic radical, saturated or containing one or more unsaturated bonds on the chain.

5. A process according to claim 2, wherein the carbonyl compound corresponds to formula (I) in which $R_a$ and $R_b$ represent an alkyl, alkenyl, alkadienyl, linear or branched radical, the hydrocarbon chain can be interrupted by one of the following groups Z:
—O—; —CO—; COO—; —NR$_1$—; —CO—NR$_1$—; —S—; —SO$_2$—; —NR$_1$—CO;

in said formulae $R_1$ represents a hydrogen atom, or a linear or branched alkyl group possessing from 1 to 6 carbon atoms, and/or it can carry one of the following substituents:
OH; —COOH; —COOX; —CO—N(R$_1$)(R$_2$); —COOR$_1$; —CHO—, —COR$_1$; —NO$_2$; —X; —CF$_3$.

in these formulae, X represents a halogen atom, and $R_2$ has the same meaning as $R_1$ given previously.

6. A process according to claim 5, wherein the carbonyl compound corresponds to formula (I) in which $R_a$ and $R_b$ represent a saturated or unsaturated, linear or branched acyclic aliphatic radical carrying a cyclic substituent, the acyclic aliphatic radical being joined to the ring by a valence bond or one of the following groups: —O—; —CO—; —COO—; —NR$_1$—; —CO—NR$_1$; —S—; —SO$_2$—; —NR$_1$—CO—.

7. A process according to claim 2, wherein the carbonyl compound corresponds to formula (I) in which $R_a$ and $R_b$ represent:

a monocyclic, heterocyclic or carbocyclic radical, saturated or containing 1 or 2 unsaturated bonds in the ring; the number of carbon atoms in the ring can vary from 3 to 8 carbon atoms, a polycyclic, heterocyclic or carbocyclic radical; the number of carbon atoms in the ring can vary from 3 to 8 carbon atoms.

8. A process according to claim 2, wherein the carbonyl compound corresponds to formula (I) in which $R_a$ and $R_b$ represent an aromatic carbocyclic radical or a benzene radical corresponding to formula (II):

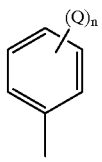

(II)

in said formula (II):

n is an integer from 0 to 5,

Q represents $R_3$, one of the following groups or functions:
a linear or branched alkyl radical, possessing from 1 to 6 carbon atoms,
a linear or branched alkenyl radical possessing from 2 to 6 carbon atoms,
a linear or branched alkoxy radical possessing from 1 to 8 carbon atoms,
an acyl group possessing from 2 to 6 carbon atoms,
a radical with the formula:

$R_5$—OH $R_5$—COOR$_7$ $R_5$—CHO $R_5$—NO$_2$ $R_5$—CN $R_5$—N(R$_7$)(R$_8$)

$R_5$—CO—N(R$_7$)(R$_8$)

$R_5$—SH $R_5$—X $R_5$—CF$_3$ in said formulae, $R_5$ represents a valence bond or a linear or branched, saturated or unsaturated divalent hydrocarbon radical, possessing from 1 to 6 carbon atoms; the radicals $R_7$ and $R_8$, which may be identical or different, represent a hydrogen atom or a linear or branched alkyl radical possessing from 1 to 6 carbon atoms; X denotes a halogen atom Q represents $R_4$, one of the following more complex radicals:

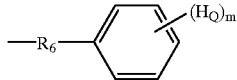

in which:
m is an integer from 0 to 5,
$R_6$ represents a valence bond-, a linear or branched, saturated or unsaturated divalent hydrocarbon group possessing from 1 to 6 carbon atoms, or one of the following groups designated Z:

—O—; —CO—; COO—; —NR$_7$—; —CO—NR$_7$—; —S—; —SO$_2$—; —NR$_7$—CO—;

in said formulae $R_7$ represents a hydrogen atom a linear or branched alkyl group possessing from 1 to 6 carbon atoms.

9. A process according to claim 2, wherein the carbonyl compound corresponds to formula (I) in which $R_a$ and $R_b$ represent:
an aromatic heterocyclic radical containing 5 or 6 atoms in the ring of which 1 or 2 are heteroatoms,
a polycyclic aromatic heterocyclic or carbocyclic radical.

10. A process according to claim 2, wherein the carbonyl compound corresponds to formula (I) in which $R_a$ represents a phenyl radical which optionally carries an alkyl or alkoxy group possessing from 1 to 4 carbon atoms, a trihalomethyl group or a halogen atom and $R_b$ represents a hydrogen atom.

11. A process according to claim 2, wherein the carbonyl compound corresponds to formula (Ia):

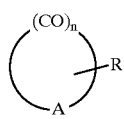

(Ia)

in which:
A denotes the residue of a ring forming all or part of a monocyclic or polycyclic system containing at least one carbonyl group,
R represents a hydrogen atom or one or more substituents, which may be identical or different,
n is a number equal to 1 or 2.

12. A process according to claim 11, wherein the carbonyl compound corresponds to formula (Ia) in which the residue A, optionally substituted, represents the residue:
of a saturated or unsaturated carbocyclic or monocyclic compound,
of a polycyclic compound containing at least two carbocycles, saturated and/or unsaturated,
of a polycyclic compound containing at least two saturated and/or unsaturated rings:
one or more of the carbon atoms being replaceable by a heteroatom,
of a polycyclic compound containing at least two carbocycles, one of which is aromatic.

13. A process according to claim 1, wherein the carbonyl compound is a carbocyclic monocyclic compound with the number of carbon atoms in the ring varying between 3 and 20 carbon atoms; said carbocycle optionally containing 1 to 2 double bonds.

14. A process according to claim 1, wherein the carbonyl compound is a polycyclic compound with the number of carbon atoms in each ring varying between 3 and 8 carbon atoms.

15. A process according to claim 1, wherein the carbonyl compound is a polycyclic compound containing at least two saturated and/or unsaturated rings: one or two of the carbon atoms being replaced by a heteroatom.

16. A process according to claim 11, wherein the carbonyl compound corresponds to formula (Ia) in which the residue A carries one or more substituents R:
R can represent $R_9$, one of the following groups:
a linear or branched, acyclic aliphatic radical, possessing from 1 to 20 carbon atoms, saturated or containing one or more unsaturated bonds on the chain; the hydrocarbon chain optionally being:

interrupted by one of the following groups designated Z:
—O—; —CO—, COO—; —NR$_{10}$—; —CO—NR$_{10}$—; —S—; —SO$_2$—;
in said formulae R$_{10}$ represents a hydrogen atom, a linear or branched alkyl radical possessing from 1 to 6 carbon atoms,
and/or carrying one of the following substituents:
OH; —CN; —N[R$_{10}$]$_2$; —COOR$_{10}$—; —CF$_3$ or —X;
in said formulae, the radicals R$_{10}$, which may be identical or different, represent a hydrogen atom, a linear or branched alkyl radical possessing from 1 to 6 carbon atoms and X represents a halogen atom,
a radical of the type =R$_{11}$, in which R$_{11}$ represents an alkylidene radical possessing from 1 to 8 carbon atoms, a radical with the formula =C(CN)$_2$ or a cycloalkylidene or cycloalkenylidene radical possessing 5 or 6 carbon atoms or a benzylidene radical, optionally substituted,
a linear or branched alkoxy radical possessing from 1 to 6 carbon atoms,
two successive atoms of the ring can be joined together by an epoxy bridge or by a bridge of the alkylene dioxy type possessing from 1 to 4 carbon atoms,
an OH group,
a COOR$_{10}$ group, R$_{10}$ representing a hydrogen atom or an alkyl radical possessing from 1 to 6 carbon atoms,
a CN group,
a halogen atom,
a —CF$_3$ group.
R can represent R$_{12}$, one of the following more complex groups:
a saturated or unsaturated carbocyclic radical possessing from 4 to 7 carbon atoms,
a radical with the formula

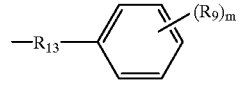

in which R$_{13}$ represents a valence bond or a linear or branched, saturated or unsaturated divalent hydrocarbon radical possessing from 1 to 6 carbon atoms, and R$_9$ has the meaning given previously and m is an integer from 0 to 4,
a radical —R$_{13}$—Z—R$_{14}$ in which Z and R$_{13}$ have the meaning given previously, R$_{14}$ represents a linear or branched alkyl radical possessing from 1 to 6 carbon atoms or a radical with the formula

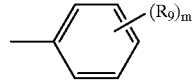

in which R$_9$ and m have the meaning given previously,
a radical of the spiro type with the formula:

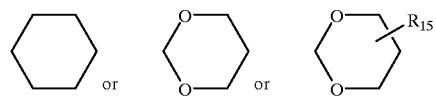

in which R$_{15}$ represents one or more linear or branched alkyl radicals possessing from 1 to 6 carbon atoms.

17. A process according to claim 11, wherein the carbonyl compound corresponds to formula (Ia) in which A is the residue of a saturated monocyclic carbocyclic compound carrying one or more substituents, a linear or branched alkyl radical possessing from 1 to 15 carbon atoms, an alkyl radical possessing from 1 to 15 carbon atoms, carrying a functional group OH, CN, N[R$_{10}$]$_2$, COOR$_{10}$ with R$_{10}$, which may be identical or different, representing a hydrogen atom, a linear or branched alkyl radical possessing from 1 to 6 carbon atoms: the alkyl chain can be interrupted by an oxygen atom or a carbonyl, carboxy or amino group, optionally substituted, and there can be mentioned a radical with the formula —NHCH$_3$ or —N(CH$_3$)$_2$, a radical with the formula —CH$_2$—CH$_2$—CN, a radical with the formula CH$_2$—CO—(CH$_2$)$_4$—COOH, a radical with the formula COCH(CH$_3$)$_2$, a radical with the formula —(CH$_2$)$_6$—COOH, a radical with the formula —CH$_2$—COOCH$_3$, a radical with the formula —CH$_2$—COOC$_2$H$_5$, a radical with the formula —CH$_2$—CH$_2$—COOCH$_3$, a radical with the formula —(CH$_2$)$_6$—COOCH$_3$, a radical with the formula —(CH$_2$)$_6$COOC$_2$H$_5$, a radical with the formula —(CH$_2$)$_5$—COOC$_2$H$_5$, a radical with the formula —CO—CH$_3$, a radical with the formula —C(CH$_3$)$_2$—CO—CH$_3$, a radical with the formula CH$_2$—CH$_2$—CO—(CH$_2$)$_4$—CH$_3$, an alkenylene or alkylidene radical, linear or branched, containing one or two double bonds possessing from 1 to 15 carbon atoms, a radical with the formula —C(CH$_3$)=CH$_2$, a radical with the formula —CH$_2$—CH=CH—C$_2$H$_5$, a radical with the formula —CH$_2$—CH=CH—(CH$_2$)$_2$—CH$_3$, a radical with the formula —CH=CH—(CH$_2$)$_4$—CH$_3$, a radical with the formula —CH$_2$CH=C(CH$_3$)$_2$, a radical with the formula —CH$_2$—CH=CCH$_3$—(CH$_2$)$_2$—CH=C(CH$_3$)$_2$, a radical =C(CH$_3$)$_2$ or =CH—(CH$_2$)$_2$—CH$_3$, an alkenylene or alkylidene radical, linear or branched, containing one or two double bonds possessing from 1 to 15 carbon atoms, carrying a functional group OH, CN, NH$_2$, COOR$_{10}$ in which R$_{10}$ has the meaning given previously: the unsaturated chain can be interrupted by an oxygen atom, a carbonyl or carboxy group and there can be mentioned a radical with the formula —CH$_2$—CH=CH—(CH$_2$)$_3$—COOH, a radical with the formula —CH=CH—C(CH$_3$)=CH—COOH, a radical with the formula —CH$_2$—CH=CH—(CH$_2$)$_3$—COOCH$_3$, a radical with the formula —CH=CH—C(CH$_3$)=CH—COOCH$_3$, a radical with the formula —CH=CH—CO—CH$_3$, a radical with the formula —CH=CH—CO—(CH$_2$)$_4$—CH$_3$ or a radical with the formula —CH=CH—CHOH—(CH$_2$)$_4$—CH$_3$, a linear or branched alkoxy radical possessing from 1 to 6 carbon atoms, two successive atoms of the ring can be joined together by an epoxy bridge or by a bridge such as the radicals methylene dioxy, ethylene dioxy, propylene dioxy, a radical of the spiro type with the formula

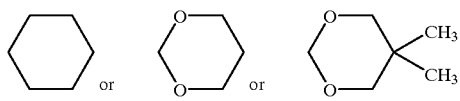

a radical with the formula

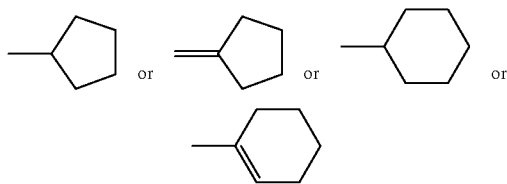

a radical with the formula

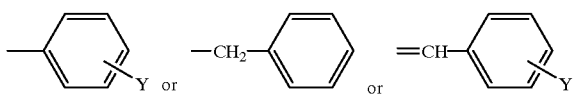

Y representing a hydrogen atom, a halogen atom, a radical with the formula

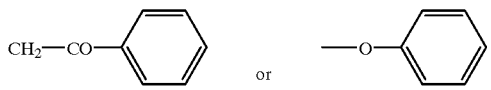

an OH group, a $COOR_{10}$ group, $R_{10}$ representing a hydrogen atom or an alkyl radical possessing from 1 to 6 carbon atoms, a CN group, a halogen atom.

18. A process according to claim 11, wherein the carbonyl compound corresponds to formula (Ia) in which A is the residue of a polycyclic carbocyclic compound, containing two saturated carbocycles carrying one or more of the following substituents:

a linear or branched alkyl radical possessing from 1 to 6 carbon atoms, a radical with the formula —$CH_2Br$, a linear or branched alkoxy radical possessing from 1 to 6 carbon atoms, a radical with the formula =$CH_2$, an OH group, a —COOH group, a halogen atom, a $CF_3$ group.

19. A process according to claim 11, wherein the carbonyl compound corresponds to formula (Ia) in which A is the residue of a bicyclic carbocyclic compound containing two carbocycles, one of which is saturated and the other is unsaturated, carrying one or more of the following substituents:

a linear or branched alkyl radical possessing from 1 to 6 carbon atoms, a radical with the formula

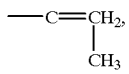

a radical with the formula —$CH_2$—O—$CH_3$, a halogen atom.

20. A process according to claim 11, wherein the carbonyl compound corresponds to formula (Ia) in which A is the residue of a polycyclic, carbocyclic compound containing two unsaturated carbocycles, carrying one or more alkyl radicals.

21. A process according to claim 11, wherein the carbonyl compound corresponds to formula (Ia) in which A is the residue of a polycyclic carbocyclic compound containing at least one aromatic carbocycle, carrying one or more of the following substituents:

a linear or branched alkyl radical possessing from 1 to 6 carbon atoms, a radical with the formula

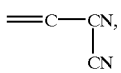

a linear or branched alkoxy radical possessing from 1 to 6 carbon atoms, a linear or branched alkoxy radical possessing from 1 to 6 carbon atoms, carrying other functional groups such as a group OH and/or $N[R_{10}]_2$ with $R_{10}$, which may be identical or different, representing a hydrogen atom, a linear or branched alkyl radical possessing from 1 to 6 carbon atoms, an OH group, an acyl group possessing from 2 to 6 carbon atoms, a group —$CH_2$—COOH, a group —$NH_2$, a halogen atom.

22. A process according to claim 1, wherein the carbonyl compound employed therefore is selected from the group consisting of the following compounds:

benzaldehyde, anisaldehyde, 4-chlorobenzaldehyde, veratric aldehyde, cinnamic aldehyde, α-naphthylaldehyde, isobornyfcyclohexanone isofenchylcyclohexanone, isocamphylcyclohexanone, bornylcyclohexanone, fenchylcyclohexanone, camphylcyclohexanone, 4-methylcyclohexanone, 4-tert-butylcyclohexanone.

23. A process according to claim 2, wherein the alcohol employed corresponds to formula (III):

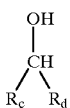

(III)

and

R$_c$ and R$_d$ have the meaning given previously for R$_a$ and R$_b$.

24. A process according to claim 23, wherein the alcohol employed is a secondary or tertiary, aliphatic or cycloaliphatic alcohol.

25. A process according to claim 23, wherein the alcohol employed is an alcohol that has less than 6 carbon atoms.

26. A process according to claim 23, wherein the alcohol employed is isopropanol, isobutanol, sec-butanol, tert-butanol or glycerol.

27. A process according to claim 1, wherein the catalyst is a natural or synthetic zeolite.

28. A process according to claim 27, wherein the zeolite is a natural zeolite selected from chabazite, clinoptilolite, erionite, mordenite, phillipsite, or offretite.

29. A process according to claim 27, wherein the zeolite is a synthetic zeolite selected from:

the synthetic zeolites with a one-dimensional network, the zeolites with a two-dimensional network, or the zeolites with a three-dimensional network, titanium-containing β zeolite, or type MCM mesoporous zeolite.

30. A process according to claim 27, wherein the zeolite is a β and Y zeolite.

31. A process according to claim 28, wherein the zeolite is employed alone or mixed with a mineral matrix comprising the oxides of metals, or alternatively from among the clays.

32. A process according to claim 1, wherein the ratio between the number of moles of carbonyl compound and the number of moles of alcohol varies between 0.1 and 20.

33. A process according to claim 1, wherein the amount of catalyst represents by weight, relative to the carbonyl compound employed, from 0.01 to 50%.

34. A process according to claim 1, wherein the temperature at which the reduction is carried out is between 20° C. and 200° C.

35. A process according to claim 1, wherein the reaction is carried out at atmospheric pressure.

36. A process according to claim 1, wherein the reaction mixture passing through the catalyst bed is sent to the reactant mixing zone to be recycled for a number of times that is sufficient to obtain the desired degree of conversion of the substrate.

37. A process according to claim 36, wherein the degree of conversion is greater than 20%.

38. A process according to claim 1, wherein the linear speed of liquid flow through the catalyst bed varies between 0.1 and 10 cm/s.

39. A process according to claim 1, wherein the dwell time of the material flow through the catalyst bed varies between 15 min and 15 h.

40. A process according to claim 1, wherein at the end of reaction, a liquid phase containing the alcohol is obtained, which can be recovered in the conventional manner.

41. In a process for reducing a carbonyl compound to the corresponding alcohol comprising the steps of reacting the carbonyl compound with an alcohol in the presence of a catalyst bed containing at least one zeolite and recovering the corresponding alcohol, the improvement which comprises recirculating the reaction mixture through the catalyst bed a sufficient number of times to achieve a desired degree of conversion of the carbonyl compound to the corresponding alcohol.

42. A process for the production of a mixture of cis and trans cyclohexanols which comprises initially forming a reaction mixture by blending in a reactor a cyclohexanone, optionally substituted with a $C_{1-12}$ alkyl group and an alcohol selected from the group consisting of isopropanol, isobutanol, sec-butanol, tert-butanol and glycerol, passing the reaction mixture from the reactor to a catalyst bed containing at least one zeolite at a temperature of 20° C. to 200° C. to reduce the cyclohexanone and recirculating the reaction mixture through the catalyst bed at least one more time to achieve a desired conversion rate.

43. A process according to claim 42, wherein the cyclohexanone is 4-methylcyclohexanone or 4-tert-butylcyclohexanone and the alcohol is isopropanol.

* * * * *